United States Patent [19]

Lorenzoni et al.

[11] Patent Number: 5,456,806
[45] Date of Patent: Oct. 10, 1995

[54] PROCEDURE FOR THE RECOVERY OF PHENOL FROM ITS MIXTURES CONTAINING CUMENE AND ALPHA-METHYLSTYRENE

[75] Inventors: Loreno Lorenzoni, Porto Torres; Giuseppe Messina, Alghero; Slavatore Simula, Ittiri, all of Italy

[73] Assignee: Enichem S.p.A., Milan, Italy

[21] Appl. No.: 232,408

[22] Filed: Apr. 25, 1994

Related U.S. Application Data

[63] Continuation of Ser. No. 62,537, May 18, 1993, abandoned.

[30] Foreign Application Priority Data

May 22, 1992 [IT] Italy .................................. 92A001247

[51] Int. Cl.⁶ ........................................................ B01D 3/40
[52] U.S. Cl. .................................. 203/62; 203/78; 203/80; 568/754
[58] Field of Search ............................ 203/62, 80, 18, 203/78, 84, DIG. 19, DIG. 9; 568/798, 335, 754

[56] References Cited

U.S. PATENT DOCUMENTS

| 3,896,006 | 7/1975 | Cooke | 203/71 |
| 4,158,611 | 6/1979 | Cooke | 203/77 |
| 4,251,325 | 2/1981 | Marsh et al. | 203/3 |
| 4,351,967 | 9/1982 | Nishimura et al. | 203/64 |
| 4,634,796 | 1/1987 | Suciu et al. | 203/36 |
| 4,851,086 | 7/1989 | Khonsari et al. | 203/39 |
| 5,122,234 | 6/1992 | Elishewitz et al. | 203/79 |
| 5,139,622 | 8/1992 | Marquis et al. | 203/78 |
| 5,240,568 | 8/1993 | Chan et al. | 293/84 |

FOREIGN PATENT DOCUMENTS

0459572  12/1991  European Pat. Off. .

OTHER PUBLICATIONS

CA 103(26) : 2159 45 t Treatment of the distillation Residue of Phenol by a Curene Prous.

Primary Examiner—Virginia Manoharan
Attorney, Agent, or Firm—Oblon, Spivak, McClelland, Maier & Neustadt

[57] ABSTRACT

A procedure for the recovery of phenol from its mixtures containing cumene and alpha-methylstyrene, is based on the extractive distillation of the mixtures with acetophenone.

9 Claims, 1 Drawing Sheet

PROCEDURE FOR THE RECOVERY OF PHENOL FROM ITS MIXTURES CONTAINING CUMENE AND ALPHA-METHYLSTYRENE

This application is a Continuation of application Ser. No. 08/062,537, filed on May 18, 1993, now abandoned.

The present invention relates to a procedure for the recovery of phenol from its mixtures containing cumene and α-methylstyrene, which is based on the extractive distillation of the mixtures with acetophenone. These mixtures are obtained in the fractional distillation and extractive distillation processes of the cleavage products of cumene hydroperoxide in the synthesis of phenol or in the cracking of tars and high-boiling products which are formed in the synthesis. The recovery of the phenol contained in these mixtures is extremely difficult due to the fact that the various components form azeotropic mixtures which are difficult to separate by distillation, and this has so far been carried out by the salification of the phenol with an alkaline solution.

Procedures are known for the production of phenol which are based on the oxidation of isopropylbenzene, otherwise known as cumene, to cumene-hydroperoxide, and the subsequent cleavage of the hydroperoxide obtained in the presence of acid catalysts; these processes are commonly defined as cumene processes, to differentiate them from other synthesis processes of phenol.

The products deriving from the acid cleavage of cumenehydroperoxide in cumene processes, after neutralization of the acid, are mainly composed of phenol and acetone and are always accompanied by smaller quantities of different by-products such as, non-reacted cumene, water, α-methylstyrene, hydroxyacetone, carboxylic acids, as well as high-boiling products such as acetophenone, cumylphenols, phenyldimethylcarbinol, dimers of α-methylstyrene and tar; part of the high-boiling products and tars are generally separated as distillation residues and cracked at temperatures of 300°–400° C. with the production of further phenol and other products among which mainly α-methylstyrene, cumene and acetophenone (DD 112,978; DD 117,869).

In any case the above reaction products are subjected to a series of distillations (U.S. Pat. Nos. 4,634,796; 4,158,611; 4,310,712; 4,333,801) suitable for separating the phenol contained therein. Generally, after a first fractionation column, suitable for separating the acetone and lower-boiling products, among which part of the non-reacted cumene, there is always a second column, called cumene column, which supplies a heavy product, practically containing all the phenol together with the high-boiling products and tars, and a light fraction composed of the azeotropic mixture mainly containing α-methylstyrene, cumene, water and phenol (about 2–7% by weight); the phenol contained in this fraction, as in azeotropic quantity, cannot be easily separated from the rest of the mixture and is generally recovered by alkaline treatment (soda), and re-acidification with sulphuric acid of the sodium phenolate thus obtained.

The heavy fraction, practically containing all of the phenol together with the high-boiling products and tars, is at this stage subjected to successive fractionation; a first treatment enables the high-boiling products and tars to be separated, to be sent to the cracking treatment with the production of further phenol. The head phenol fraction thus obtained (crude phenol), still containing α-methylstyrene as an impurity, is purified by extractive distillation using a suitable solvent, (JP 49/27564; GB 824,595; U.S. Pat. Nos. 3.169.101; 4,166.772; 4.271.322).

Also in this purification step, as well as the heavy fraction containing almost all the phenol, a light fraction is obtained containing phenol, α-methylstyrene and hydroxyacetone which is difficult to separate and must be treated with soda.

Generally the treatment with soda (or with other bases) is also carried out on cracked high-boiling products (see above) (U.S. Pat. Nos. 4,634,796; 3,692,845; 4,298,765; 4,559,110) and precisely on the azeotropic fractions deriving from the fractional distillation of the products which contain cumene, α-methylstyrene and phenol, and which, for the reasons already stated, are also difficult to separate in other ways.

From an analysis of the known art it can be deduced that, both in the fractional distillation of the products obtained from the acid cleavage of cumene hydroperoxide, and the extractive distillation of fractions rich in phenol but still containing considerable impurities, as also the fractional distillation of the cracking products of the high-boiling residues and tars deriving from the previous treatments, fractions containing cumene, α-methylstyrene and water are always obtained, which are difficult to separate and necessitate alkaline treatment. The removal of the phenol from these mixtures is particularly necessary in that, (U.S. Pat. No. 4.333.801) if the cumene is to be recycled (hydrogenated α-methylstyrene also supplies cumene) to the synthesis oxidative process of cumenehydroperoxide, it has to be freed from the phenol which accompanies it and which, as is known, is a strong inhibitor of oxidation. Treatment with soda however has a few disadvantages; among these, i) the high consumption of soda which increases the production costs, ii) the necessity of disposing of the sodium sulphate which is formed in the subsequent acidification with sulphuric acid and which must be removed from the mother liquor before their discharge, iii) the necessity of having a unit for water treatment which can dispose of the phenol contained in the aqueous solution of sodium sulphate.

A process has recently been proposed (U.S. Pat. No. 4.333,801) for the separation of the phenol from its mixtures containing cumene and α-methylstyrene based on the formation of a phenol water phase which is removed from the bottom of the distillation column and a poorer phase of water and phenol which is removed from the top. This process however is suited only to fractions which cannot contain heavy products as the phenol is obtained as a heavy fraction and would contain these products; infact, as shown in the same patent (U.S. Pat. No. 4.333.801), the process is suitable for the treatment of fractions coming from the distillation column of cumene, and is not suitable for the recovery of phenol contained in the fractions, containing cumene and/or α-methylstyrene, but coming from the cracking of high-boiling products and tars mentioned above. In addition, the process disclosed in U.S. Pat. No. 4,333,801 cannot be applied for the treatment of streams containing reasonably high quantities of hydroxyacetone and other impurities which would be collected together with the phenol.

The present invention therefore relates to a general method for the recovery of phenol from streams containing it together with cumene, α-methylstyrene and water and which can only be separated by treatment with soda.

The present invention also relates to a flexible method for the recovery of phenol from fractions containing it together with cumene and α-methylstyrene, wherein tars and/or other hydrocarbons higher-boiling than phenol and wherein the phenol can be contained in greater quantities and proportions, may also be present.

This method basically consists in sending the mixture to be treated and containing varying quantities of phenol to extractive distillation with acetophenone, which is a by-product of the production process of phenol starting from cumene hydroperoxide, and which is normally eliminated with the high-boiling products; for this reason the acetophenone always accompanies the phenol fractions coming from the cracking of the high-boiling products and tars and must not be added to the mixture to be treated when the recovery of phenol relates to these fractions.

Extractive distillation with acetophenone, although using a completely different operating procedure, has already been advantageously applied to the purification of phenol (see above), guaranteeing a better quality of the product (IT 20514/A90).

In accordance with this, a first aspect of the present invention relates to a process for the recovery of phenol from streams which contain it together with fractions of cumene and α-methylstyrene, consisting in subjecting these streams to extractive distillation in the presence of acetophenone, this process being characterized by the following operations:

a) continuously feeding this mixture into a first distillation column (C1) operating under extractive conditions, at an intermediate point above which the extracting agent, coming from the bottom of a second column (C2) and basically composed of a mixture of acetophenone and phenol, is fed, b) continuously removing from the top of the first distillation column (C1), and collecting in a separator (D1), a mixture of low-boiling products, containing practically all of the cumene, α-methylstyrene and water present in the feeding mixture and traces of phenol (less than 0.5% by weight), and which is separated in the separator (D1) in an aqueous phase and organic phase, c) recovering part of the organic phase, contained in the mixture of low-boiling products and separated in the separator (D1), and sending the remaining part back to the head of the first column (C1), at a point which is lower than the outlet of the mixture of low-boiling products and higher than the inlet of the extracting agent, d) continuously removing from the bottom of the first distillation column an organic mixture rich in phenol, basically composed of acetophenone and phenol, e) feeding into an intermediate point of the second column (C2), the organic mixture rich in phenol removed from the bottom of the first column (C1), f) continuously taking from the bottom of the second column (C2), an organic mixture poor in phenol and basically composed of acetophenone and phenol, g) removing a small part of the organic mixture poor in phenol withdrawn from the bottom of the second column (C2), h) sending the majority of the organic mixture poor in phenol withdrawn from the bottom of the second column (C2), back into an intermediate point of the first distillation column (C1), to function as an extracting agent, i) continuously taking from the top of the second column (C2) and collecting in an accumulator (D2) basically pure phenol, l) continuously recycling a part of the phenol collected in the accumulator (D2) to the column (C2) and precisely to a point in the upper part of the column (C2).

Figure 1:
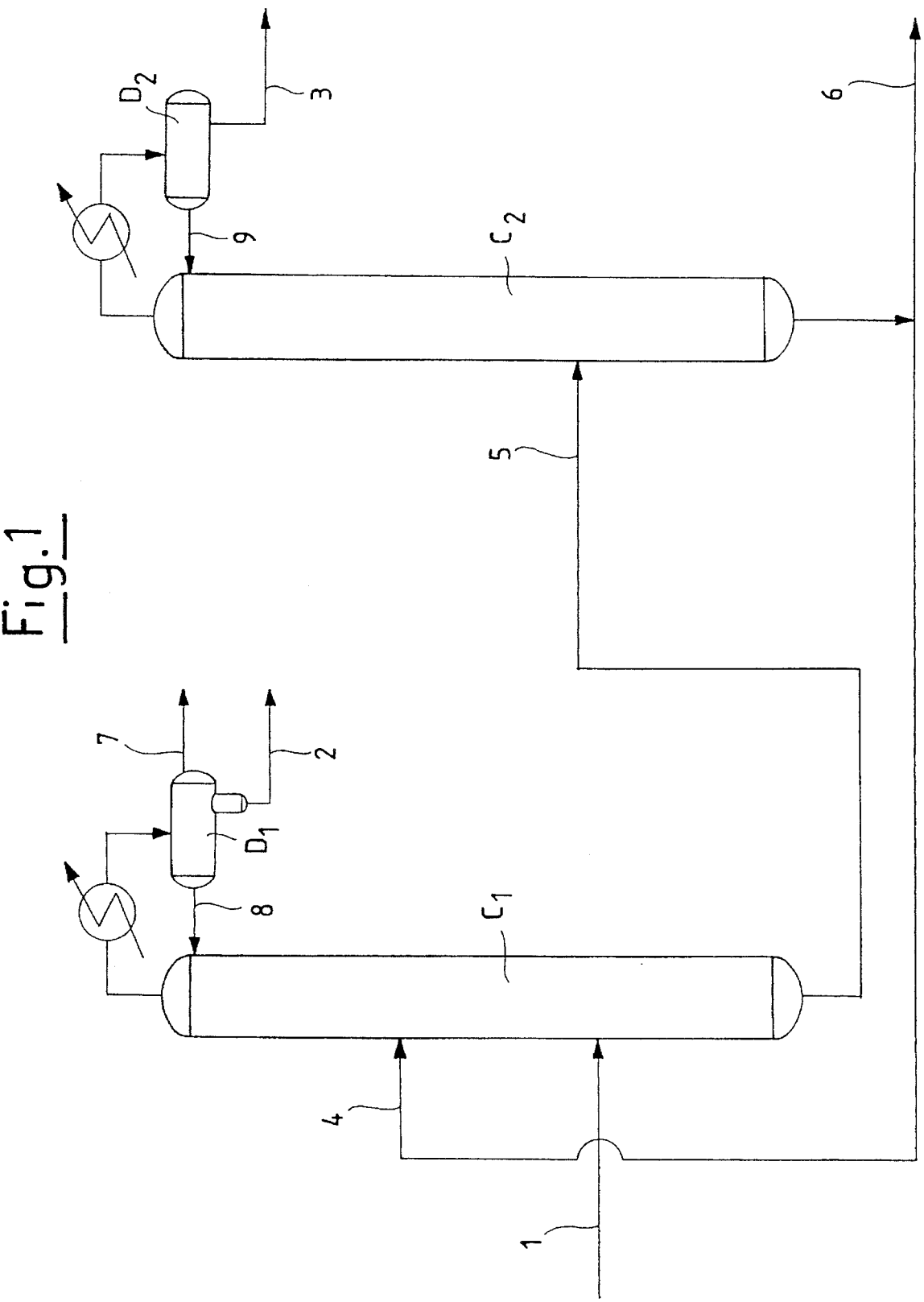
FIG. 1 shows the preferred operating scheme of the extractive distillation plant according to the present invention.

A major characteristic of the procedure for the recovery of phenol according to the present invention, which differentiates it from the other procedures of extractive distillation of the known art, is the fact of operating on streams with varying degrees of phenol, which contain it together with hydrocarbons such as cumene and α-methylstyrene, which form azeotropic mixtures which can only be separated by treatment with alkalies.

The procedure according to the invention can therefore, for the above reasons, also be applied to the streams of phenol to which the fractions recovered from the cracking of the high-boiling products and which also contain cumene and α-methylstyrene, have been added.

A point which characterizes the present invention is the use of acetophenone as an extracting agent, in that, this extracting agent is able to break the azeotropic mixture of phenol with cumene and α-methylstyrene and water.

A further advantage of the procedure of the present invention is that, owing to the breakage of the equilibrium of the pre-existing azeotropic mixtures on the part of the acetophenone, any possible hydroxyacetone and part of the low-boiling organic acids contained in the feeding mixture, which would otherwise (without extractive distillation in the presence of acetophenone) leave the bottom of the first column (C1) together with the phenol, are also separated from the top of the first distillation column (C1), together with the water contained in the feeding mixture.

The process of the present invention is also characterized by its flexibility and facility of adaptation to the compositions and characteristics of the phenol streams being fed (% of phenol, different ratios cumene/α-methylstyrene, concentration of acetophenone in the feeding mixture). Acetophenone is an inexpensive product because it is a by-product of the synthesis of phenol and can therefore be modulated as desired when added to the feeding mixture; the acetophenone, once the plant is under steady conditions, is kept in the plant at the desired concentration to carry out its extracting function, by means of the continuous discharging of part of the organic mixture poor in phenol withdrawn from the bottom of the second column (C2); with this discharge it is also possible to remove any high-boiling products and tars present in the feeding mixture.

With all the above characteristics, it is easy to deduce that, using the recovery process of phenol from its mixtures with cumene and α-methylstyrene according to the present invention, a rigorous separation of most of the phenol and high-boiling products, before entering the plant, is no longer necessary, in that the process can be easily adapted even to considerable variations in the composition of the streams being fed.

With the recovery process of phenol according to the present invention, the phenol obtained, which returns to the primary fractionation of the plant, has no hydroacetone and contains few low-boiling organic acids.

The description of the preferred embodiment of the recovery process of phenol of the present invention refers to FIG. 1, enclosed with the present invention, which shows the operating scheme of the extractive distillation plant. This plant can operate both under atmospheric pressure and super-atmospheric or sub-atmospheric pressure; this operating method can also apply to the single columns. Infact, the first distillation column (C1) can operate at both atmospheric and sub-atmospheric pressure, with a preference for sub-atmospheric pressure (50–300 tor), whereas the second column (C2) can operate at atmospheric pressure or sub-atmospheric or super-atmospheric pressure with a preference for pressures close to atmospheric pressure.

The scheme shown in FIG. 1 has been simplified and is only aimed at illustrating the operating method for the process of the present invention and should not be considered a limitation for the purposes of the invention. The missing equipment such as pumps, valves, compressors, heat-exchangers, and also the control instruments have been omitted as they are not essential for understanding the invention.

With reference to the scheme of FIG. 1, a stream coming from the synthesis plant of phenol from cumene, containing α-methylstyrene, acetophenone, cumene and water as the main by-products, and also containing a quantity of impurities, hydroxyacetone (about 2000 ppm) and traces of $C_1$–$C_5$ aliphatic carboxylic acids, is fed by line (1) into an intermediate point of a distillation column (C1).

The extracting agent basically composed of the mixture of acetophenone and phenol poor in phenol and coming from the bottom of the subsequent column (second distillation column) (C2) is fed through line (4) to column (C1), which operates under extracting conditions. The weight ratio acetophenone/phenol of this mixture which is poor in phenol, leaving the bottom of the second column is between that of the azeotropic mixture under operating conditions and that of a mixture richer in phenol with respect to the azeotropic value; in practice this ratio is between the values 9 and 4.

Operating under these conditions, a mixture of products basically composed of cumene and α-methylstyrene, containing all the hydroxyacetone, water and most of the aliphatic carboxylic acids is extracted from the head of the first distillation column (C1); this mixture, after condensation in a condenser, is separated in the separator (D1) in an organic phase and aqueous phase. Part of the organic phase is recycled, through line 8, to the head of the first distillation column (C1), whereas the other part is sent for storage through line 7 and the aqueous phase, containing hydroxyacetone, organic acids and traces of cumene and α-methylstyrene, is sent, through line 2, for purifying treatment before being discharged.

A mixture rich in phenol, basically composed of acetophenone and phenol (with traces of cumene and possible high-boiling products) is continuously withdrawn from the bottom of column (C1), and is sent, through line 5, to the following column (C2).

Phenol is recovered from the head of column (C2), after condensation in the accumulator (D2), which is partly refluxed, through line 9, to the head of column (C2), whereas the remaining part is continuously withdrawn from (D2) and sent for storage through line 3.

A mixture poor in phenol and composed of acetophenone and phenol in the above ratios is continuously withdrawn from the bottom of the second distillation column (C2). Part of this mixture poor in phenol is recovered and removed from the process through line 6; this removal is a characteristic of the process which makes it extremely flexible and prevents the accumulation of acetophenone and other heavy products contained in the feeding mixture.

The two columns used in the extractive distillation process of the present invention are normal fractional distillation columns, which are made to function under extraction conditions in a countercurrent of acetophenone; they can have plates or packing and their dimensions vary according to the volumes being used as known in the art; considering the types of streams being treated, they have a theoretical plate number generally of between 10 and 100.

The feeding mixture is charged in an intermediate point of the first distillation column (C1), which is at a height of between 1/10 and 5/10 of the total height of the column; the extracting mixture, coming from the bottom of the second column (C2) and basically composed of acetophenone and phenol is, however, fed above this point and precisely in an intermediate point between the inlet of the feeding mixture and that of the recycled organic phase composed of low-boiling products coming from the separator (D1) (see above).

The mixture of acetophenone and phenol, rich in phenol which is continuously withdrawn from the bottom of the first column (C1), is introduced in an intermediate point of the second column (C2) which, functioning as a simple distillation column, can be easily calculated according to the criteria of the known art.

In a typical procedure of extractive distillation of the present invention, the composition of the mixture rich in phenol taken from the bottom of the first distillation column (C1), is such that the weight ratio acetophenone/phenol is between the values 4 and 1; instead, the composition of the mixture poor in phenol, taken from the bottom of the second column (C2), most of which is introduced with the function of an extracting mixture in an intermediate point of the first distillation column (C1), is basically composed of acetophenone and phenol in a weight ratio acetophenone/phenol of between 4 and 9.

The following examples provide a better understanding of the present invention but do not limit it in any way.

EXAMPLE 1

With reference to FIG. 1, a stream coming from the phenol plant is fed to column (C1) through line (1), and has the following composition:

| | |
|---|---|
| cumene | 5.96% by weight |
| α-methylstyrene | 42.72% by weight |
| water | 1.68% by weight |
| hydroxyacetone | 0.2% by weight |
| phenol | 39.46% by weight |
| acetophenone | 9.98% by weight |

The plant functions with the first column operating at 100 mm of Hg and the second column operating at atmospheric pressure. With the plant under steady conditions there is the following balance:

| | |
|---|---|
| feeding | 1510 g/hr |
| aqueous phase recovered from line (2) | about 25 g/hr |
| organic phase recovered from line (7) | about 735 g/hr |
| phenol recovered from line (3) | about 560 g/hr |
| mixture phenol + acetophenone + tars recovered from line (6) | about 190 g/hr |
| TOTAL RECOVERED | 1510 g/hr |

1405 g/hr of an organic phase are collected in the separator (D1) under standard conditions, of which 735 g/hr are recovered and 670 g/hr (49% of the total) are recycled to the head of the first column (C1).

5910 g/hr of phenol are collected in the accumulator (D2), of which 5350 g/hr (90.5% of the total) are recycled to the head of the second distillation column (C2) through line (9).

A flow of acetophenone and phenol equal to 3190 g/hr is taken from the bottom of column (C2), of which 3000 g/hr (94.5% of the total mixture removed) are recycled to the first column (C1) through line (4). The composition of the mixture taken from the bottom of the column (C2) is the following:

| | | |
|---|---|---|
| acetophenone | 78.1% | |
| phenol | 18.4% | |
| tars | 3.5% | | ratio acetophenone/phenol 4.25.

A mixture of acetone and phenol, rich in phenol and having a ratio acetophenone/phenol of 2.17 is sent from the bottom of the first column (C1), through line (5), to the second column (C2).

All the low-boiling hydrocarbons which contain 1400 ppm of phenol and practically all the water contained in the feeding mixture are recovered from the head of the first column (C1); in the aqueous phase hydroxyacetone (8.5%) and 1350 ppm of phenol are also present.

The phenol recovered from line (7) contains at least 20 ppm of hydroxyacetone.

EXAMPLE 2

The same procedure is carried out as in example 1. With reference to FIG. 1, a stream coming from the phenol plant and having the following composition is fed to column (C1) through line (1):

| | |
|---|---|
| cumene | 20.78% by weight |
| α-methylstyrene | 24.29% by weight |
| water | 1.68% by weight |
| hydroxyacetone | 0.2% by weight |
| phenol | 40.25% by weight |
| acetophenone | 12.8% by weight. |

The plant functions with the first column operating at 100 mm of Hg and the second column operating at atmospheric pressure. With the plant under standard conditions there is the following balance:

| | |
|---|---|
| feeding | 1510 g/hr |
| aqueous phase recovered from line (2) | about 25 g/hr |
| organic phase recovered from line (7) | about 673 g/hr |
| phenol recovered from line (3) | about 563 g/hr |
| mixture phenol + acetophenone + tars recovered from line (6) | about 247 g/hr |
| TOTAL RECOVERED | 1508 g/hr |

1323 g/hr of an organic phase are collected in the separator (D1) under standard conditions, of which 673 g/hr are recovered and 650 g/hr (49% of the total) are recycled to the head of the first column (C1).

5933 g/hr of phenol are collected in the accumulator (D2), of which 5370 g/hr (90.5% of the total) are recycled to the head of the second distillation column (C2) through line (9).

A flow of acetophenone and phenol equal to 3247 g/hr is taken from the bottom of column (C2), of which 3000 g/hr (92% of the total mixture removed) are recycled to the first column (C1) through line (4) and 247 g/hr are recovered through line (6). The composition of the mixture taken from the bottom of the column (C2) is the following:

| | |
|---|---|
| acetophenone | 78.3% |

-continued

| | |
|---|---|
| phenol | 18.4% |
| tars | 3.3% | ratio acetophenone/phenol 4.25.

3809 g/hr of a mixture of acetone and phenol, rich in phenol and having the following composition are sent from the bottom of the first column (C1), through line (5), to the second column (C2):

| | |
|---|---|
| acetophenone | 66.7% by weight |
| phenol | 30.5% by weight |
| tars | 2.8% by weight |

(ratio acetophenone/phenol = 2.19).

The low-boiling hydrocarbons which contain 200 ppm of phenol and practically all of the water contained in the feeding mixture are recovered from the head of the first column (C1); in the aqueous phase hydroxyacetone (8.93%) and 180 ppm of phenol are also present.

The phenol recovered from line (7) contains at least 20 ppm of hydroxyacetone.

EXAMPLE 3

The same procedure is carried out as in example 1. With reference to FIG. 1, a stream coming from the phenol plant and having the following composition is fed to column (C1) through line (1):

| | |
|---|---|
| cumene | 33.55% by weight |
| α-methylstyrene | 32.4% by weight |
| water | 1.68% by weight |
| hydroxyacetone | 0.2% by weight |
| phenol | 21.4% by weight |
| acetophenone | 10.77% by weight. |

The plant functions with the first column operating at 100 mm of Hg and the second column operating at atmospheric pressure. With the plant under standard conditions there is the following balance:

| | |
|---|---|
| feeding | 1302 g/hr |
| aqueous phase recovered from line (2) | about 22 g/hr |
| organic phase recovered from line (7) | about 851 g/hr |
| phenol recovered from line (3) | about 250 g/hr |
| mixture phenol + acetophenone + tars recovered from line (6) | about 174 g/hr |
| TOTAL RECOVERED | 1297 g/hr |

1501 g/hr of an organic phase are collected in the separator (D1) under standard conditions, of which 851 g/hr are recovered and 650 g/hr (43% of the total) are recycled to the head of the first column (C1).

3790 g/hr of phenol are collected in the accumulator (D2), of which 3540 g/hr (93.5% of the total) are recycled to the head of the second distillation column (C2) through line (9).

A flow of acetophenone and phenol equal to 3249 g/hr is taken from the bottom of column (C2), of which 3000 g/hr (92% of the total mixture removed) are recycled to the first column (C1) through line (4). The composition of the mixture poor in phenol taken from the bottom of the second column (C2) is the following:

| | | |
|---|---|---|
| acetophenone | 80.5% | |
| phenol | 16.5% | |
| tars | 3.0% | | ratio acetophenone/phenol 4.88.

3429 g/hr of a mixture of acetone and phenol, rich in phenol and having a ratio acetone/phenol of 3.3 and a content of high-boiling products and tars of 2.8% are sent from the bottom of the first column (C1), through line (5), to the second column (C2):

The low-boiling hydrocarbons which contain 80 ppm of phenol and practically all of the water contained in the feeding mixture are recovered from the head of the first column (C1); in the aqueous phase hydroxyacetone (5.76%) and 65 ppm of phenol are also present.

The phenol recovered from line (7) contains at least 20 ppm of hydroxyacetone.

EXAMPLE 4

Using the same procedure as in the previous samples, 670 g/hr of a stream having the following composition are fed to the first column (C1):

| | | |
|---|---|---|
| cumene | 21.7% | by weight |
| α-methylstyrene | 24.5% | by weight |
| water | 1.5% | by weight |
| hydroxyacetone | 0.2% | by weight |
| phenol | 40.2% | by weight |
| acetophenone | 11.9% | by weight. |

A flow of acetophenone and phenol equal to 3000 g/hr and containing 78.2% of acetophenone, 15.67% of phenol and 6.13% of tars is recycled from the bottom of column (C2) to (C1).

The organic reflux at (C1) is fixed at 700 g/hr whereas the reflux of phenol at the head of column (C2) is equal to 3500 g/hr.

With the plant under steady conditions it is found that:

the organic phase recovered at the head of column (C1) contains less than 20 ppm of phenol;

the water recovered from the head of column (C1) contains 8.22% of hydroxyacetone and less than 20 ppm of phenol;

the phenol obtained from the head of column (C2) contains less than 20 ppm of hydroxyacetone.

We claim:

1. Process for the recovery of phenol from a stream containing 21.4 to 40.2 wt. % phenol together with water and fractions of cumene and α-methylstyrene, consisting in subjecting the streams to extractive distillation in the presence of acetophenone, consisting essentially of the steps:

a) continuously feeding said stream into a first distillation column (C1) operating under extractive distillation conditions, at an intermediate point above which an extracting agent, coming from the bottom of a second column (C2) consisting essentially of a mixture of acetophenone and phenol, is fed, b) continuously removing from the top of the first distillation column (C1), and collecting in a separator (D1), a mixture of low-boiling products, containing substantially all of the cumene, α-methylstyrene, the water present in said stream and traces of phenol, separating said mixture of low-boiling products in the separator (D1) into an aqueous phase and an organic phase, c) recovering part of the organic phase, present in the mixture of low-boiling products and separated in the separator (D1), and sending the remaining part back to the head of the first distillation column (C1), at a point which is lower than the outlet of the mixture of low-boiling products and higher than the inlet of the extracting agent, d) continuously removing from the bottom of the first distillation column an organic mixture consisting essentially of acetophenone and mainly phenol, e) feeding into an intermediate point of the second column (C2), the organic mixture removed from the bottom of the first column (C1), f) continuously taking from the bottom of the second column (C2), an organic mixture consisting essentially of phenol and mainly acetophenone, g) removing a small part of the organic mixture taken from the bottom of the second column (C2), h) sending the majority of the organic mixture taken from the bottom of the second column (C2), back to an intermediate point of the first distillation column (C1), to function as extracting agent, i) continuously withdrawing from the top of the second column (C2) and collecting essentially phenol in an accumulator (D2), l) continuously recycling a part of the phenol collected in the accumulator (D2) to the distillation column (C2) to a point in the upper part of the distillation column (C2).

2. Process according to claim 1, wherein the remaining part of the organic phase which is sent back from the separator (D1) to the head of the first distillation column (C1), constitutes from $4/10$ to $7/10$ of the total organic phase, coming from the head of the first distillation column (C1) and separated in the separator (D1).

3. Process according to claim 1, wherein the mixture taken from the bottom of the second column (C2), most of which is introduced to function as extracting agent in an intermediate point of the first distillation column (C1), consists essentially of phenol and mainly acetophenone in a weight ratio of acetophenone and phenol of between 4 and 9.

4. Process according to claim 1, wherein the mixture which is removed from the bottom of the second distillation column (C2) and fed into an intermediate point of the first distillation column (C1), constitutes from $80/100$ to $98/100$ of the total of said mixture.

5. Process according to claim 1, wherein the mixture removed from the bottom of the first distillation column (C1) and fed into an intermediate point of the second column (C2), consists essentially of acetophenone and mainly phenol in a weight ratio of acetophenone and phenol of between 1 and 4.

6. Process according to claim 1, wherein the part of phenol collected in the accumulator (D2) which is recycled to the head of the second column (C2) constitutes from $80/100$ to $95/100$ of the total phenol collected.

7. Process according to claim 1, wherein said first distillation column (C1) is operated at atmospheric pressure.

8. Process according to claim 1, wherein said first distillation column (C1) is operated at sub-atmospheric pressure.

9. Process according to claim 1, wherein said first distillation column (C1) is operated at 50–300 torr.

* * * * *